United States Patent
Zhang et al.

(10) Patent No.: US 12,270,058 B2
(45) Date of Patent: Apr. 8, 2025

(54) FERULOYL ESTERASE AND APPLICATION THEREOF

(71) Applicant: Jiangnan University, Wuxi (CN)

(72) Inventors: Tao Zhang, Wuxi (CN); Bo Jiang, Wuxi (CN); Xiaoli Duan, Wuxi (CN); Ming Miao, Wuxi (CN)

(73) Assignee: Jiangnan University, Wuxi (CN)

( * ) Notice: Subject to any disclaimer, the term of this patent is extended or adjusted under 35 U.S.C. 154(b) by 727 days.

(21) Appl. No.: 17/485,682

(22) Filed: Sep. 27, 2021

(65) Prior Publication Data

US 2022/0002689 A1 Jan. 6, 2022

Related U.S. Application Data

(63) Continuation of application No. PCT/CN2020/119269, filed on Sep. 30, 2020.

(30) Foreign Application Priority Data

Aug. 31, 2020 (CN) .......................... 202010898408.0
Aug. 31, 2020 (CN) .......................... 202010900348.1
Sep. 29, 2020 (CN) .......................... 202011048393.5

(51) Int. Cl.
*C12N 9/18* (2006.01)
*C12P 7/42* (2006.01)

(52) U.S. Cl.
CPC .................. *C12N 9/18* (2013.01); *C12P 7/42* (2013.01); *C12Y 301/01073* (2013.01)

(58) Field of Classification Search
CPC ...... C12N 9/18; C12P 7/42; C12Y 301/01073
See application file for complete search history.

(56) References Cited

U.S. PATENT DOCUMENTS

2011/0053213 A1* 3/2011 Joergensen .... C12Y 301/01073
435/41

FOREIGN PATENT DOCUMENTS

CN 106434598 A 2/2017
EP 3186373 A1 7/2017

OTHER PUBLICATIONS

Zeigler, Daniel R., et al. "The origins of 168, W23, and other Bacillus subtilis legacy strains." Journal of bacteriology 190.21 (2008): 6983-6995. (Year: 2008).*
Duan, Xiaoli, Yiwei Dai, and Tao Zhang. "Characterization of feruloyl esterase from Bacillus pumilus SK52. 001 and its application in ferulic acid production from de-starched wheat bran." Foods 10.6 (2021): 1229. (Year: 2021).*
Holmquist, Mats. "Alpha beta-hydrolase fold enzymes structures, functions and mechanisms." Current Protein and Peptide Science 1.2 (2000): 209-235. (Year: 2000).*
Zhou, Cheng, Yanfen Xue, and Yanhe Ma. "Characterization and high-efficiency secreted expression in Bacillus subtilis of a thermo-alkaline β-mannanase from an alkaliphilic Bacillus clausii strain S10." Microbial Cell Factories 17 (2018): 1-19. (Year: 2018).*
Weiyue Liang et al., "A novel feruloyl esterase with high rosmarinic acid hydrolysis activity from Bacillus pumilus W3", International Journal of Biological Macromolecules 161 (Jun. 9, 2020) 525 530.

* cited by examiner

*Primary Examiner* — Robert J Yamasaki
*Assistant Examiner* — Trevor Kane
(74) *Attorney, Agent, or Firm* — IPRO, PLLC (57) ABSTRACT

The disclosure discloses a feruloyl esterase and application thereof, and belongs to the technical field of microorganisms. The disclosure provides a feruloyl esterase with an amino acid sequence shown in SEQ ID NO: 2 and specific enzyme activity as high as 519 U/g. The disclosure provides a recombinant *Bacillus subtilis* which uses *Bacillus subtilis* as a host, expresses a gene encoding the feruloyl esterase with an amino acid sequence shown in SEQ ID NO: 2, and can be used for producing the feruloyl esterase with a high yield. The process specifically includes inoculating a fermentation culture medium with the recombinant *Bacillus subtilis* for fermentation for 14 hours, and the enzyme activity of the feruloyl esterase in a cell disruption supernatant can be as high as 82.53 U/mL.

4 Claims, 4 Drawing Sheets

Specification includes a Sequence Listing.

SEQUENCE LISTING

<160> NUMBER OF SEQ ID NOS: 5

<210> SEQ ID NO 1
<211> LENGTH: 1404

```
<212> TYPE: DNA
<213> ORGANISM: Bacillus pumilus

<400> SEQUENCE: 1
tgcaagtcga gcgaacagaa gggagcttgc tcccggatgt tagcggcgga cgggtgagta      60
acacgtgggt aacctgcctg taagactggg ataactccgg gaaaccggag ctaataccgg     120
atagttcctt gaaccgcatg gttcaaggat gaaagacggt ttcggctgtc acttacagat     180
ggacccgcgg cgcattagct agttggtggg gtaatggctc accaaggcga cgatgcgtag     240
ccgacctgag agggtgatcg gccacactgg gactgagaca cggcccagac tcctacggga     300
ggcagcagta gggaatcttc cgcaatggac gaaagtctga cggagcaacg ccgcgtgagt     360
gatgaaggtt ttcggatcgt aaagctctgt tgttagggaa gaacaagtgc gagagtaact     420
gctcgcacct tgacggtacc taaccagaaa gccacggcta actacgtgcc agcagccgcg     480
gtaatacgta ggtggcaagc gttgtccgga attattgggc gtaaagggct cgcaggcggt     540
ttcttaagtc tgatgtgaaa gcccccggct caaccgggga gggtcattgg aaactgggaa     600
acttgagtgc agaagaggag agtggaattc cacgtgtagc ggtgaaatgc gtagagatgt     660
ggaggaacac cagtggcgaa ggcgactctc tggtctgtaa ctgacgctga ggagcgaaag     720
cgtggggagc gaacaggatt agataccctg gtagtccacg ccgtaaacga tgagtgctaa     780
gtgttagggg gtttccgccc cttagtgctg cagctaacgc attaagcact ccgcctgggg     840
agtacggtcg caagactgaa actcaaagga attgacgggg cccgcacaa gcggtggagc      900 atgtggttta attcgaagca acgcgaagaa ccttaccagg tcttgacatc ctctgacaac     960
cctagagata gggctttccc ttcggggaca gagtgacagg tggtgcatgg ttgtcgtcag    1020
ctcgtgtcgt gagatgttgg gttaagtccc gcaacgagcg caaccccttga tcttagttgc    1080 cagcatttag ttgggcactc taaggtgact gccggtgaca aaccggagga aggtggggat    1140
gacgtcaaat catcatgccc cttatgacct gggctacaca cgtgctacaa tggacagaac    1200
aaagggctgc gagaccgcaa ggtttagcca atcccataaa tctgttctca gttcggatcg    1260
cagtctgcaa ctcgactgcg tgaagctgga atcgctagta atcgcggatc agcatgccgc    1320
ggtgaatacg ttcccgggcc ttgtacacac cgcccgtcac accacgagag tttgtaacac    1380
ccgaagtcgg tgaggtaacc ttta                                           1404

<210> SEQ ID NO 2
<211> LENGTH: 297
<212> TYPE: PRT
<213> ORGANISM: Bacillus pumilus

<400> SEQUENCE: 2

Met Asn Leu Gln Glu Gln Ile Lys Ile Ala Ala Ser Leu Arg Gln Pro
1               5                   10                  15

Ala Glu Gly Ser Leu Pro Ser Gln Ser Glu Leu Lys Pro Val His Pro
                20                  25                  30

Pro Glu Val Asn Lys Met Glu Tyr Asp Ile Pro Thr Ser Ala Gly Glu
            35                  40                  45

Thr Lys Val Trp Ile Phe Lys Pro Val Asn Thr Ser Lys Gln Pro Leu
        50                  55                  60

Pro Val Phe Val Asn Leu His Gly Gly Gly Phe Ile Leu Gly Ser Ala
65                  70                  75                  80

Glu Met Asp Asn His Trp Cys Pro Val Ile Ala Asp Arg Ala Gln Cys
                85                  90                  95
```

```
Ile Val Val Asn Val Glu Tyr Gln Leu Ala Pro Glu His Pro Phe Pro
                100                 105                 110

Ala Ala Leu His Glu Cys Tyr Asp Val Leu Lys Trp Leu Tyr Glu His
        115                 120                 125

Pro Asp Glu Leu Gln Ile Asp Pro Asn Arg Val Ala Ile Gly Gly His
    130                 135                 140

Ser Ala Gly Gly Asn Leu Ala Thr Ala Ala Cys Leu Leu Asn Ile Gln
145                 150                 155                 160

Lys Gly Asn Pro Val Pro Ile Val Tyr Gln Val Leu Asp Tyr Pro Pro
                165                 170                 175

Leu Asp Leu Ala Thr Asp Pro Ala Glu Lys Pro Ala Phe Glu Glu Ala
            180                 185                 190

Ile Pro Val Glu Met Ala Arg Leu Phe Asn Ala Phe Tyr Leu Gln Gly
        195                 200                 205

Gln Asp Pro His Asn Pro Leu Val Ser Pro Ile Phe Ala Asp Arg Ser
    210                 215                 220

Ser Leu Ala Gln Leu Pro Pro Ala Leu Val Ile Thr Ala Glu Arg Asp
225                 230                 235                 240

Ser Leu Ala Gln Glu Ala Glu Gln Tyr Ala Glu Lys Leu Lys Glu Ala
                245                 250                 255

Gly Val Asp Val Thr Tyr Arg Gln Phe Lys Gly Val Pro His Ala Phe
            260                 265                 270

Thr His Ala Gly Asp Leu Glu Ile Ala Glu Glu Ala Trp His Leu Met
        275                 280                 285

Ser Asp Gln Leu Lys Lys Ala Phe Glu
    290                 295
```

<210> SEQ ID NO 3
<211> LENGTH: 894
<212> TYPE: DNA
<213> ORGANISM: Bacillus pumilus

<400> SEQUENCE: 3

```
atgaacttac aagagcaaat caaaatcgct gcgtcattac gtcaaccggc tgaaggttca    60
ttaccgagtc aatcggaact aaaaccagtc catcctcccg aagtgaacaa atggaatat    120
gacattccaa caagtgctgg cgaaacaaag gtatggatat taagccggt caacacatca    180
aagcagccgc ttcccgtttt tgtgaattta catggcggag gatttatcct aggcagtgct    240
gaaatggata ccactggtgt ccggtcatt gcagaccgag cgcaatgtat cgtcgtcaat    300
gtcgagtatc agcttgcccc agagcaccct tttccagcag ctcttcatga atgctacgat    360
gtgctgaagt ggctgtatga acaccctgat gagcttcaaa tagatcctaa tagagtagcc    420
attggcggac atagtgcagg aggaaacttg caacggctg cttgtctctt aaatattcaa    480
aaagggaacc cagtcccgat tgtctatcaa gtgcttgatt atccgccgct tgatttagcc    540
actgatccag cagaaaagcc agcatttgaa gaagcgatcc cagttgaaat ggcgaggctc    600
tttaatgcct tctatctgca aggccaagat ccgcacaatc cgctcgtttc tccaatcttt    660
gccgatcgtt catccttggc tcaactgcca ccagctctcg ttatcacagc tgaaagagat    720
tcgctagctc aagaagccga acaatatgcg gagaagttaa agaagcagg ggtagatgtc    780
acgtacagac agtttaaagg agtccctcac gccttcacgc atgctggaga tttagaaata    840
gctgaagaag cttggcatct gatgagtgat caattgaaaa aggcatttga ataa          894
```

<210> SEQ ID NO 4

```
<211> LENGTH: 53
<212> TYPE: DNA
<213> ORGANISM: Artificial Sequence
<220> FEATURE:
<223> OTHER INFORMATION: Synthetic DNA

<400> SEQUENCE: 4
aaaaggagcg atttacatat gatgaactta caagagcaaa tcaaaatcgc tgc    53

<210> SEQ ID NO 5
<211> LENGTH: 55
<212> TYPE: DNA
<213> ORGANISM: Artificial Sequence
<220> FEATURE:
<223> OTHER INFORMATION: Synthetic DNA

<400> SEQUENCE: 5
gagctcgact ctagaggatc cttaatggtg atggtgatga tgttcaaatg ccttt   55
```

FERULOYL ESTERASE AND APPLICATION THEREOF

TECHNICAL FIELD

The disclosure relates to a feruloyl esterase and application thereof, and belongs to the technical field of microorganisms.

BACKGROUND

Ferulic acid (FA), widely contained in plant cell walls, is connected with polysaccharides, cellulose and lignin through ester bonds or ether bonds to form complex network skeleton structures in the cell walls, so as to maintain the integrity of the cell walls, and at the same time, the biodegradation rate is reduced.

Ferulic acid, recognized as a safe antioxidant in the world, is listed in food additives in Japan, the United States and other countries. In addition, ferulic acid also has the effects of ultraviolet absorption, bacteria and inflammation resistance, cancer prevention, blood fat reduction and the like, and has a broad application prospect in the fields of medicine, cosmetics, papermaking and the like.

At present, methods for producing ferulic acid mainly include a plant extraction method, a chemical synthesis method and a biological enzyme method. According to the plant extraction method, natural ferulic acid is mainly extracted and separated from *angelica sinensis, Coptis chinensis*, rice bran, wheat bran and other plants through an acid-base hydrolysis method. However, other chemical components in the cell walls are changed by using the acid-base hydrolysis method. Therefore, other high-value chemical components in plants are destroyed by using this method to produce ferulic acid. Meanwhile, there are many by-products when ferulic acid is produced by using the acid-base hydrolysis method, products are difficult to separate. Moreover, consumption of energy is high when ferulic acid is produced by using this method, and the environment is polluted. According to the chemical synthesis method, vanillin is mainly used as a base raw material to produce ferulic acid through a series of organic reactions. However, since the product is doped with cis-ferulic acid, the separation cost is increased by using this method to produce ferulic acid. In addition, ferulic acid produced by using this method cannot be directly used as a pharmaceutical raw material. Besides, there are also disadvantages of long reaction time and serious environmental pollution during production of ferulic acid by using this method.

According to the biological enzyme method, a feruloyl esterase (ferulic acid esterase, FAE, EC 3.1.1.73) is mainly added into a reaction system containing a ferulic acid ester compound for a reaction to produce ferulic acid. Compared with the acid or base hydrolysis method and the chemical synthesis method, production of ferulic acid by using the biological enzyme method has the advantages of mild reaction conditions, high specificity and environmental friendliness. Due to these advantages, the biological enzyme method becomes a hot spot of research on production of ferulic acid.

SUMMARY

The disclosure discloses a feruloyl esterase, and an amino acid sequence of the feruloyl esterase is shown in SEQ ID NO: 2.

The disclosure also discloses a gene encoding the above feruloyl esterase.

In an embodiment of the disclosure, a nucleotide sequence of the gene is shown in SEQ ID NO: 3.

The disclosure also discloses a recombinant plasmid carrying the above gene.

In an embodiment of the disclosure, an expression vector of the recombinant plasmid is a pMA5 plasmid, a pUB plasmid or a pTSC plasmid.

The disclosure also discloses a microbial cell carrying the above gene or the above recombinant plasmid.

In an embodiment, the microbial cell is *Bacillus pumilus* or *Bacillus subtilis*.

In an embodiment, the *Bacillus subtilis* is *Bacillus subtilis* 168, *Bacillus subtilis* WB800, *Bacillus subtilis* WB600 or *Bacillus subtilis* 1A751.

The disclosure also discloses a method for producing the feruloyl esterase, and the method includes first inoculating a fermentation culture medium with the above microbial cell for fermentation to obtain a fermentation solution, and then separating the feruloyl esterase from the fermentation solution.

The disclosure also discloses application of the above microbial cell or the above method for producing the feruloyl esterase in production of the feruloyl esterase.

The disclosure also discloses a method for producing ferulic acid, and the method includes first adding the feruloyl esterase into a reaction system containing a ferulic acid ester compound for a reaction to obtain a reaction solution, and then separating ferulic acid from the reaction solution;

or, the method includes first inoculating a fermentation culture medium with the above microbial cell for fermentation to obtain a fermentation solution, separating the feruloyl esterase from the fermentation solution, adding the feruloyl esterase into a reaction system containing a ferulic acid ester compound for a reaction to obtain a reaction solution, and finally separating ferulic acid from the reaction solution;

or, the method includes first inoculating a fermentation culture medium with the above microbial cell for fermentation to obtain a fermentation solution, adding the fermentation solution into a reaction system containing a ferulic acid ester compound for a reaction to obtain a reaction solution, and finally separating ferulic acid from the reaction solution.

In an embodiment, the ferulic acid ester compound is methyl ferulate, ethyl ferulate or a raw material containing a ferulic acid ester.

In an embodiment, the reaction temperature is 30-90° C., and the time is 10-30 minutes.

The disclosure also discloses application of the above feruloyl esterase, the above gene, the above recombinant plasmid, the above microbial cell or the above method in production of ferulic acid, hydrolysis of lignocellulose, food, medicine, feed and papermaking.

The disclosure has the following beneficial effects:

(1) The disclosure discloses a feruloyl esterase with an amino acid sequence shown in SEQ ID NO: 2 and specific enzyme activity as high as 519 U/g. Therefore, the feruloyl esterase has a great application prospect in production of ferulic acid.

(2) The disclosure discloses a recombinant *Bacillus subtilis* which uses *Bacillus subtilis* as a host, expresses the gene encoding the feruloyl esterase with an amino acid sequence shown in SEQ ID NO: 2, and can be used for producing the feruloyl esterase with a high yield. The process specifically includes inoculating a fermentation culture medium with the recombinant *Bacillus subtilis* for fermentation for 14 hours, and the enzyme activity of the feruloyl esterase is as high as 82.53 U/mL. Therefore, the recombinant *Bacillus subtilis* has a great application prospect in production of the feruloyl esterase and ferulic acid.

Preservation of Biological Materials

A *Bacillus pumilus* SK52.001, taxonomically named *Bacillus pumilus*, has been preserved in China Center for Type Culture Collection on Aug. 14, 2020, the preservation number is CCTCC NO: M 2020421, and the preservation address is Wuhan University, Wuhan, China.

DETAILED DESCRIPTION

A ferulic acid standard product involved in the following examples is purchased from Beijing Bailingwei Technology Co., Ltd.; methyl ferulate involved in the following examples is purchased from Alfa Aesar (China) Chemical Co., Ltd.; bovine albumin and coomassie brilliant blue G-250 involved in the following examples are purchased from Shanghai Sinopharm Chemical Reagent Co., Ltd.; a pMA5 plasmid involved in the following examples is purchased from YouBio; *Escherichia coli* DH5α involved in the following examples is purchased from General Biological Co., Ltd.; *Bacillus subtilis* WB800 involved in the following examples is purchased from National Type Culture Collection (NTCC); a lysozyme involved in the following examples is purchased from Sangon Biotech (Shanghai) Co., Ltd.; tris(hydroxymethyl)aminomethane (Tris) and disodium ethylenediaminetetraacetate dihydrate involved in the following examples are purchased from Shanghai Macklin Biochemical Co., Ltd.

Culture Media Involved in the Following Examples are as Follows:

A culture medium for strain isolation includes 200 g/L potato, 20 g/L sucrose and 15 g/L agar, and the pH is natural.

A culture medium for solid screening is obtained by filtering an N,N-dimethylformamide solution containing 100 mg/L ethyl ferulate with a 0.22 μm filter membrane to obtain an ethyl ferulate solution, cooling a sterilized basic culture medium to 60° C., adding 10% (v/v) of the ethyl ferulate solution into the basic culture medium and shaking the solution uniformly until the solution becomes a uniform milky white solution.

The basic culture medium includes 2 g/L $NaNO_3$, 1 g/L $K_2HPO_4 \cdot 3H_2O$, 0.5 g/L KCl, 0.5 g/L $MgSO_4 \cdot 7H_2O$, 0.01 g/L $FeSO_4 \cdot 7H_2O$ and 15 g/L agar, and the pH is natural.

A seed culture medium includes 200 g/L potato and 20 g/L sucrose, and the pH is natural.

A basic fermentation culture medium includes 20 g/L wheat bran, 2 g/L $NaNO_3$, 1 g/L $K_2HPO_4 \cdot 3H_2O$, 0.5 g/L KCl, 0.5 g/L $MgSO_4 \cdot 7H_2O$ and 0.01 g/L $FeSO_4 \cdot 7H_2O$, and the pH is natural.

An LB liquid culture medium includes 10 g/L tryptone, 5 g/L yeast extract and 10 g/L sodium chloride, and the pH is natural.

An LB solid culture medium includes 10 g/L tryptone, 5 g/L yeast extract, 10 g/L sodium chloride and 15 g/L agar powder.

A Super Rich culture medium includes 25 g/L tryptone, 20 g/L yeast extract, 3.0 g/L dipotassium hydrogen phosphate and 30 g/L glucose, and the pH is natural.

Solutions Involved in the Following Examples are as Follows:

1. A lysis solution includes 6.057 g/L Tris and 5.844 g/L NaCl, the pH is adjusted to 8.0 with hydrochloric acid, and the lysis solution is diluted to 1 L.
2. A dialysis solution includes 6.057 g/L Tris, the pH is adjusted to 8.0 with hydrochloric acid, and the dialysis solution is diluted to 1 L.
3. The enzyme activity of a feruloyl esterase is defined as that the amount of an enzyme required to decompose methyl ferulate to produce 1 μmol ferulic acid per minute at 50° C. is 1 enzyme activity unit (1 U).

A calculation formula of the activity of the feruloyl esterase is as follows:

activity of feruloyl esterase=(dilution multiple*concentration of ferulic acid*volume of reaction system)/(reaction time*relative molecular mass of ferulic acid*volume of added enzyme solution).

Figure 3:
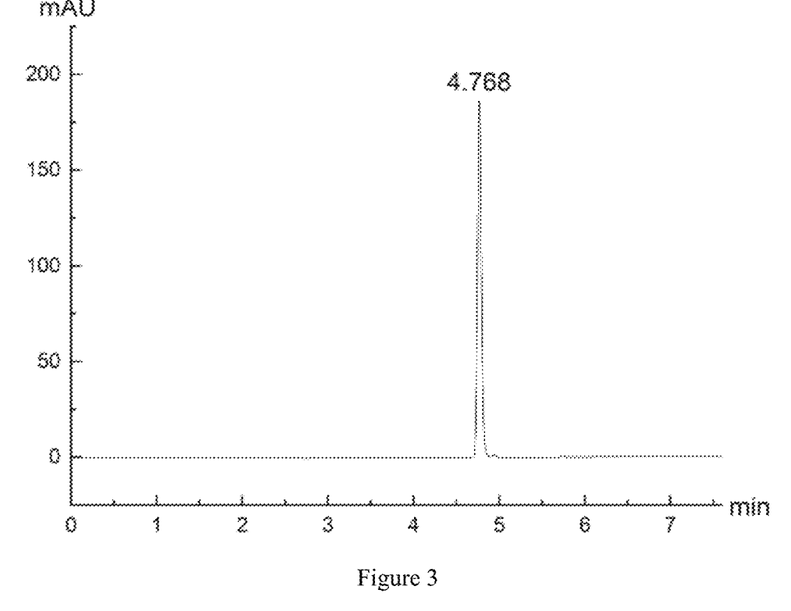
FIG. 3 is a high performance liquid chromatogram of a ferulic acid standard product.
Figure 4:
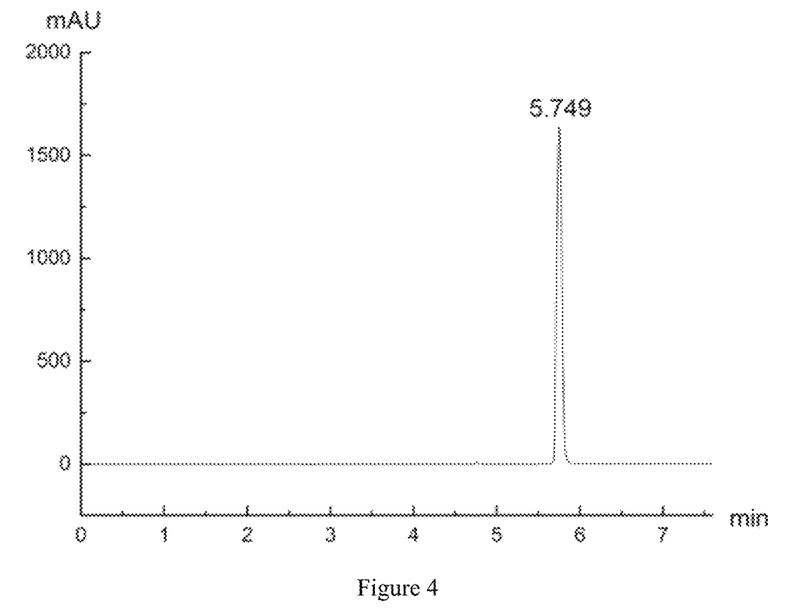
FIG. 4 is a high performance liquid chromatogram of a methyl ferulate standard product.
Figure 5:
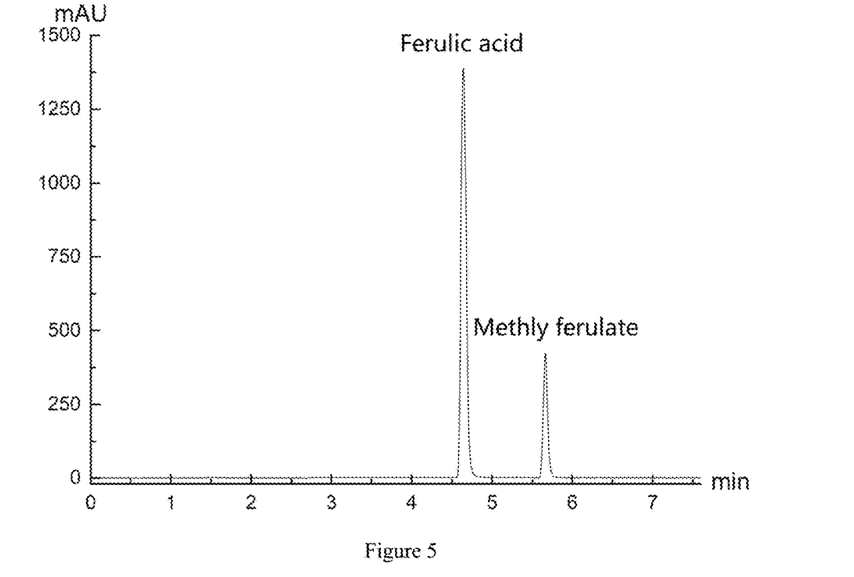
FIG. 5 is a high performance liquid chromatogram of a reaction solution.

A high performance liquid chromatogram of a ferulic acid standard product is shown in FIG. 3, a high performance liquid chromatogram of a methyl ferulate standard product is shown in FIG. 4, a high performance liquid chromatogram of a reaction solution is shown in FIG. 5, and the concentration of ferulic acid is calculated based on a linear relationship Y=52514X−80.417 ($R^2$=0.9996) between the peak area Y and the concentration X of ferulic acid in the high performance liquid chromatogram.

4. An HPLC method is used: An Agilent 1 200 high performance liquid chromatograph is used; ZORBAX Eclipse Plus C18 (Agilent, 4.6 mm*150 mm, 3.5 μm) is used as a chromatographic column; an ultraviolet detector is used; a mobile phase A is a 1% (v/v) acetic acid solution, and a mobile phase B is methanol; the flow rate is 1 mL/min; the column temperature is 30° C.; the detection wavelength is 320 nm, and a gradient elution procedure is shown in Table 1.

TABLE 1

| Elution procedure | | |
|---|---|---|
| Time/min | A phase/% | B phase/% |
| 0 | 90 | 10 |
| 0.23 | 70 | 30 |
| 1.66 | 50 | 50 |
| 4.97 | 0 | 100 |
| 5.57 | 85 | 15 |
| 7.52 | 90 | 10 |
| 7.60 | 90 | 10 |

5. A method for detecting the yield of ferulic acid in a reaction solution is as follows:

The reaction solution is first subjected to enzyme deactivation with boiling water for 10 minutes and then filtered with a 0.22 µm membrane, a crude enzyme solution obtained after enzyme deactivation is used as a blank control, and the concentration of ferulic acid in the reaction solution is detected by HPLC (high performance liquid chromatography).

Example 1: Obtaining of *Bacillus pumilus* SK52.001

Specific steps are as follows:
1. Isolation and Purification of *Bacillus pumilus* SK52.001

Soil derived from a Gonghu bay wetland area in Wuxi, Jiangsu province was used as a sample, 1.0 g of the sample was added into 10 mL of sterile water filled with glass beads, and the mixture was subjected to oscillation in a shaker at 30° C. and 200 r/min for 30 minutes to make bacterial cells fully separated, so as to obtain a mixed bacterial solution; 0.5 mL of the mixed bacterial solution was sucked into a 10 mL centrifuge tube filled with 4.5 mL of normal saline in a sterile environment to obtain a $10^{-1}$ diluent, and the dilution step above was repeated to sequentially obtain a $10^{-2}$ diluent, a $10^{-3}$ diluent, a $10^{-4}$ diluent, a $10^{-5}$ diluent and a $10^{-6}$ diluent; 100 µL of the diluents with dilution gradients of $10^{-3}$, $10^{-4}$, $10^{-5}$ and $10^{-6}$ were separately sucked, spread on a culture medium for strain isolation and subjected to inverted culture in a constant-temperature incubator at 30° C. for 24-48 hours to obtain diluted spread plates; single colonies on the diluted spread plates were picked, streaked on a culture medium for solid screening and subjected to inverted culture in the constant-temperature incubator at 30° C. for 24 hours to obtain single colonies; whether there were transparent circles around the single colonies was observed, and the single colonies with transparent circles around were screened; one single colony was screened this time, and a strain corresponding to the single colony was named SK52.001.
2. Identification of *Bacillus pumilus* SK52.001

A genome of the strain SK52.001 was extracted, 16S rDNA of the strain SK52.001 was subjected to amplification and sequencing (completed by Tianyi Huiyuan Biotechnology Co., Ltd.), a 16S rDNA sequence of the strain SK52.001 obtained after sequencing analysis (the 16S rDNA sequence of SK52.001 is shown in SEQ ID NO: 1) was compared in GenBank, and it was shown through results that the strain was *Bacillus pumilus* and named *Bacillus pumilus* SK52.001.
3. Observation of *Bacillus pumilus* SK52.001

Figure 1:
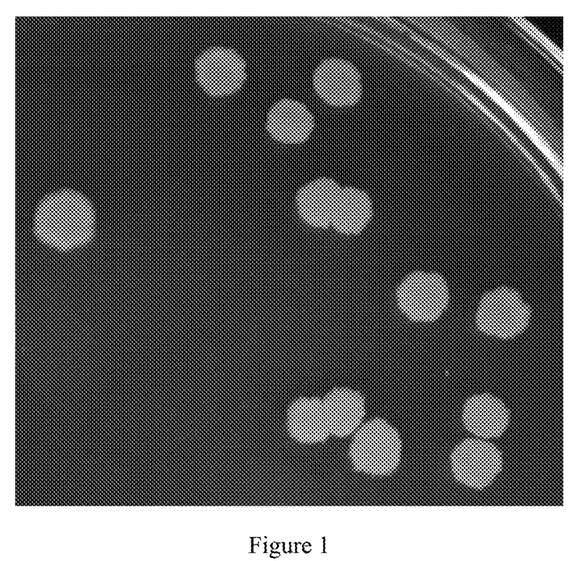
FIG. 1 shows the colony morphology of *Bacillus pumilus* SK52.001.
Figure 2:
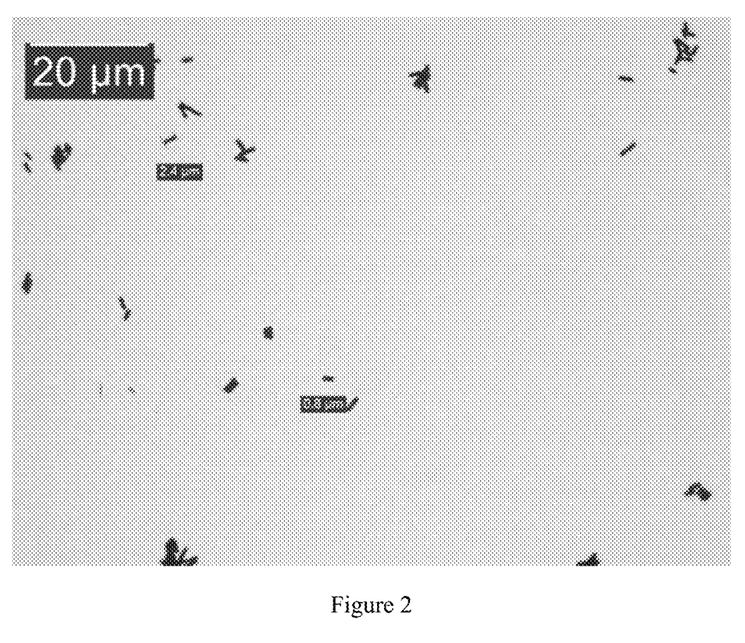
FIG. 2 shows the bacterial cell morphology of *Bacillus pumilus* SK52.001.

A bacterial solution of *Bacillus pumilus* SK52.001 was streaked on an LB solid culture medium and subjected to inverted culture in a constant-temperature incubator at 30° C. for 12 hours to obtain a single colony; the single colony was picked, and an LB liquid culture medium was inoculated with the single colony for culturing in a shaker at 30° C. and 200 r/min for 12 hours to obtain a bacterial solution; the bacterial solution was diluted 100 times with sterile water, spread on an LB solid culture medium and then cultured in an incubator at 30° C. for 18 hours, and the colony morphology was observed (the colony morphology is shown in FIG. 1); the bacterial solution was diluted 20 times with sterile water and observed under an optical microscope, and the bacterial cell morphology was observed (the bacterial cell morphology is shown in FIG. 2).

It can be seen from FIG. 1 that the colony morphology of *Bacillus pumilus* SK52.001 is that *Bacillus pumilus* SK52.001 is round, thin, light yellow in the middle, white at the edges, viscous and moist on the surface and uneven at the edges.

It can be seen from FIG. 2 that the bacterial cell morphology of *Bacillus pumilus* SK52.001 is that *Bacillus pumilus* SK52.001 is short rod-shaped and rounded at both ends, has typical morphological characteristics of *Bacillus* and belongs to gram-positive bacteria.

Example 2: Production of a Feruloyl Esterase

Specific steps are as follows:
A seed culture medium was inoculated with a single colony of *Bacillus pumilus* SK52.001 obtained in Example 1 for culturing in a shaker at 30° C. and 200 r/min for 18 hours to obtain a seed solution; a basic fermentation culture medium was inoculated with the seed solution according to an inoculation amount of 5% (v/v) for fermentation in a shaker at 30° C. and 200 r/min for 26 hours to obtain a fermentation solution.

The fermentation solution is centrifuged at 4° C. and 10,000 rpm for 10 minutes to obtain a crude enzyme solution; the enzyme activity of the feruloyl esterase in the crude enzyme solution is detected, and a detection method is as follows:

250 µL of the crude enzyme solution was added into 750 µL of a methyl ferulate solution with a concentration of 0.003 mol/L to obtain an enzyme reaction system (the methyl ferulate solution was obtained by dissolving methyl ferulate in a Tris-HCl buffer solution with a pH of 8.0 and a concentration of 0.05 mol/L); the enzyme reaction system was subjected to a reaction in a water bath pot at 50° C. for 30 minutes and enzyme deactivation with boiling water for 10 minutes and then filtered with a 0.22 µm membrane to obtain a reaction solution; the crude enzyme solution obtained after enzyme inactivation was used as a blank control, and the concentration of ferulic acid in the reaction solution was detected by HPLC (high performance liquid chromatography); the concentration of ferulic acid was substituted into a calculation formula of the activity of the feruloyl esterase to obtain the enzyme activity of the feruloyl esterase in the crude enzyme solution.

According to detection results, the enzyme activity of the feruloyl esterase in the crude enzyme solution is 195 U/L.

Figure 6:
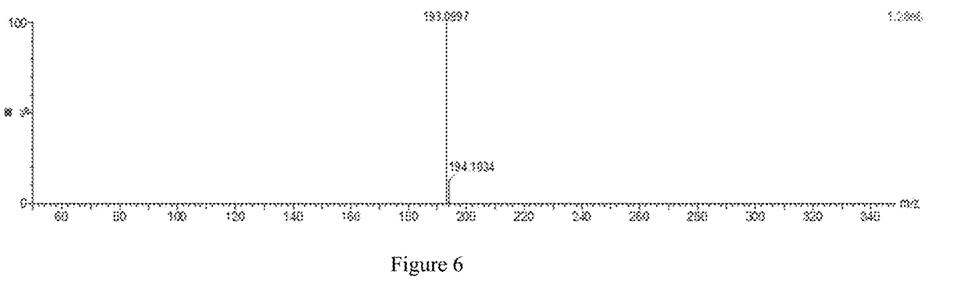
FIG. 6 is an LC-MS diagram of a reaction solution.

In order to further prove that *Bacillus pumilus* SK52.001 can produce the feruloyl esterase, the reaction solution is analyzed by LC-MS (analysis results are shown in FIG. 6).

It can be seen from FIG. 6 that a fragment with the highest relative abundance of product peaks is shown as m/z=193, and the relative molecular mass of a target product is 194, which is consistent with the relative molecular weight of a ferulic acid monomer.

Example 3: Production of a Feruloyl Esterase

Specific steps are as follows:
On the basis of Example 1, the basic fermentation culture medium was separately replaced with fermentation culture media A-E to obtain fermentation solutions A-E.

The fermentation culture medium A includes 45 g/L wheat bran, 5 g/L tryptone, 1.0 g/L $K_2HPO_4·3H_2O$, 0.5 g/L KCl, 0.5 g/L $MgSO_4·7H_2O$ and 0.01 g/L $FeSO_4·7H_2O$, and the pH is 6.0.

The fermentation culture medium B includes 10 g/L starch-removed wheat bran, 2 g/L $NaNO_3$, 1.0 g/L $K_2HPO_4·3H_2O$, 0.5 g/L KCl, 0.5 g/L $MgSO_4·7H_2O$ and 0.01 g/L $FeSO_4·7H_2O$, and the pH is natural. A treatment method of the starch-removed wheat bran includes: soaking wheat bran in a potassium acetate solution with a concentration of 0.3% (w/w) to obtain a mixture, constantly stirring the mixture in a water bath at 95° C. for 1 hour, repeatedly rinsing the mixture with deionized water until starch was completely removed and then drying the mixture at 105° C. to reach a constant weight for later use.

The fermentation culture medium C includes 10 g/L wheat bran, 2 g/L NaNO$_3$, 1.0 g/L K$_2$HPO$_4$·3H$_2$O, 0.5 g/L KCl, 0.5 g/L MgSO$_4$·7H$_2$O and 0.01 g/L FeSO$_4$·7H$_2$O, and the pH is natural.

The fermentation culture medium D includes 45 g/L wheat bran, 2 g/L NaNO$_3$, 1.0 g/L K$_2$HPO$_4$·3H$_2$O, 0.5 g/L KCl, 0.5 g/L MgSO$_4$·7H$_2$O and 0.01 g/L FeSO$_4$·7H$_2$O, and the pH is natural.

The fermentation culture medium E includes 45 g/L wheat bran, 5 g/L yeast extract, 1.0 g/L K$_2$HPO$_4$·3H$_2$O, 0.5 g/L KCl, 0.5 g/L MgSO$_4$·7H$_2$O and 0.01 g/L FeSO$_4$·7H$_2$O, and the pH is natural.

The fermentation solutions A-E were separately centrifuged at 4° C. and 10,000 rpm for 10 minutes to obtain crude enzyme solutions A-E; the enzyme activity of the feruloyl esterase in the crude enzyme solutions A-E was detected; according to detection results, the enzyme activity of the feruloyl esterase in the crude enzyme solutions A-E was separately 421 U/L, 73 U/L, 102 U/L, 241 U/L and 344 U/L. It can be seen that when the fermentation culture medium A is used, the yield of the feruloyl esterase from *Bacillus pumilus* SK52.001 is the highest.

Example 4: Performance of a Feruloyl Esterase

Figure 7:
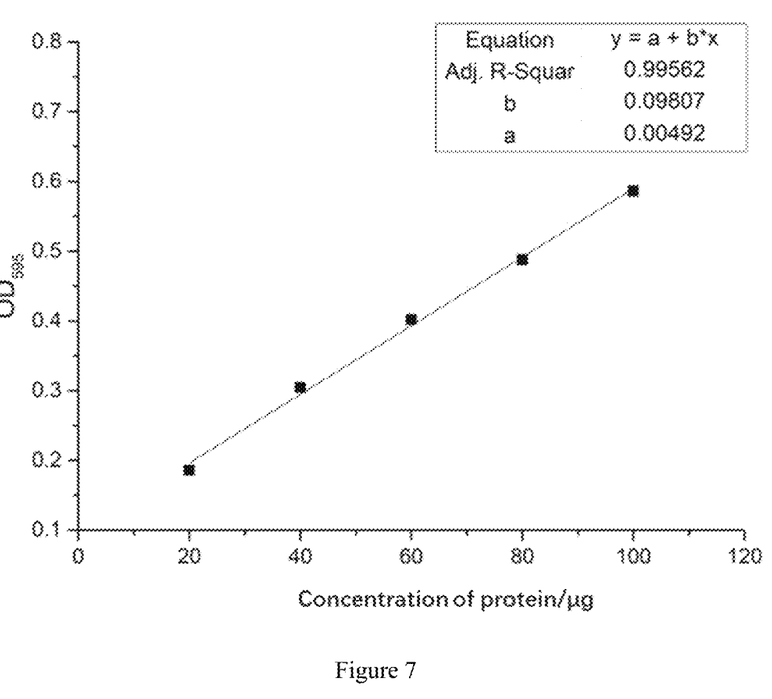
FIG. 7 shows a protein concentration standard curve.

Specific steps are as follows:
The specific enzyme activity of the feruloyl esterase in a crude enzyme solution A is detected, and a detection method is as follows:

100 mg of coomassie brilliant blue G-250 was weighed and dissolved in 50 mL of 90% (v/v) ethanol, 100 mL of 85% (v/v) phosphoric acid was added, and the mixture was diluted with distilled water to 1 L to obtain a coomassie brilliant blue G-250 dyeing solution; 100 mg of bovine albumin was weighed, dissolved and diluted with distilled water to 100 mL to obtain a standard protein solution; 0, 0.02, 0.04, 0.06, 0.08 and 0.10 mL of the standard protein solution were sucked and added into 1.0, 0.98, 0.96, 0.94, 0.92 and 0.90 mL of distilled water respectively, and 5 mL of the coomassie brilliant blue G-250 dyeing solution was separately added into the solutions and mixed uniformly to obtain mixed solutions; the mixed solutions were subjected to a reaction at 25° C. for 2 minutes to obtain reaction solutions; the absorbance of the reaction solutions was detected at a wavelength of 595 nm, and a protein concentration standard curve was drawn (the standard curve is shown in FIG. 7).

100 μL of the crude enzyme solution A obtained in Example 2 was diluted with distilled water to 1 mL to obtain a diluent; 5 mL of the coomassie brilliant blue G-250 dyeing solution was added into the diluent and mixed uniformly to obtain a mixed solution; the mixed solution was subjected to a reaction at 25° C. for 2 minutes to obtain a reaction solution; the absorbance of the reaction solution was detected at a wavelength of 595 nm; the concentration of protein in the crude enzyme solution A was calculated based on the detected absorbance and the protein concentration standard curve, and the specific enzyme activity of the feruloyl esterase in the crude enzyme solution A was calculated based on the concentration of protein in the crude enzyme solution A.

A calculation formula of the specific enzyme activity of the feruloyl esterase is as follows:

specific enzyme activity=enzyme activity of crude enzyme solution/concentration of protein.

According to detection results, the concentration of protein in the crude enzyme solution A is 0.81 mg/mL, and the specific enzyme activity of the feruloyl esterase in the crude enzyme solution A is 519 U/g.

A genome of *Bacillus pumilus* SK52.001 is subjected to PCR amplification to obtain a gene of the feruloyl esterase, and the gene is subjected to sequencing; according to sequencing results, the amino acid sequence of the feruloyl esterase in the crude enzyme solution A is shown in SEQ ID NO: 2, and the nucleotide sequence of the gene encoding the feruloyl esterase in the crude enzyme solution A is shown in SEQ ID NO: 3.

Example 5: Production of Ferulic Acid

Specific steps are as follows:
A seed culture medium was inoculated with a single colony of *Bacillus pumilus* SK52.001 obtained in Example 1 for culturing in a shaker at 30° C. and 200 r/min for 18 hours to obtain a seed solution; a basic fermentation culture medium was inoculated with the seed solution according to an inoculation amount of 5% (v/v) and fermented in a shaker at 30° C. and 200 r/min for 40 hours to obtain a fermentation solution; the fermentation solution was continuously sampled during fermentation; the sampled fermentation solution was centrifuged at 4° C. and 10,000 rpm for 10 minutes to obtain a crude enzyme solution; 250 μL of the crude enzyme solution was added into 750 μL of a methyl ferulate solution with a concentration of 0.003 mol/L to obtain an enzyme reaction system (the methyl ferulate solution was obtained by dissolving methyl ferulate in a Tris-HCl buffer solution with a pH of 8.0 and a concentration of 0.05 mol/L); the enzyme reaction system was subjected to a reaction in a water bath pot at 50° C. for 30 minutes to obtain a reaction solution.

The yield of ferulic acid in the reaction solution was detected.

Figure 8:
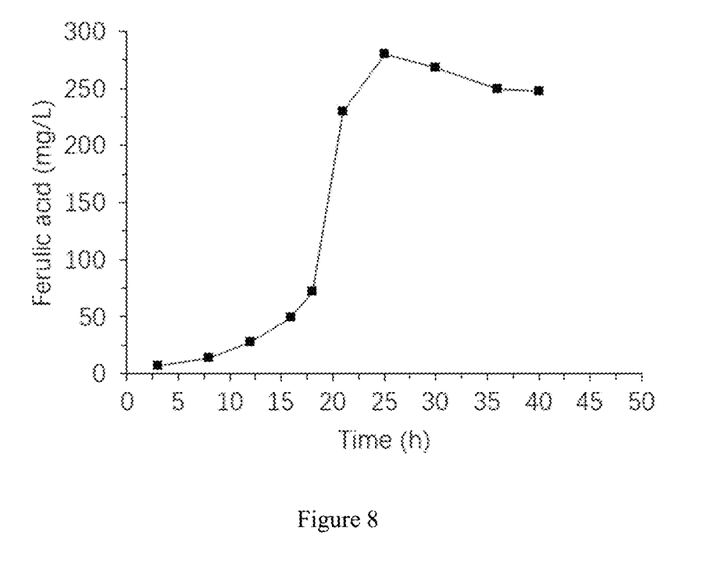
FIG. 8 shows the yield of ferulic acid in a reaction solution.

According to results shown in FIG. 8, after the crude enzyme solution obtained after fermentation for 26 hours is subjected to a reaction for 30 minutes, the yield of ferulic acid is 280 mg/L.

Example 6: Construction of Recombinant *Bacillus subtilis*

Specific steps are as follows:
A genome of *Bacillus pumilus* SK52.001 obtained in Example 1 was used as a template, fae-F and fae-R were used as primers, and a gene encoding a feruloyl esterase (SEQ ID NO: 3) was obtained by PCR amplification; the gene encoding the feruloyl esterase and a pMA5 plasmid were ligated by using a homologous recombinase Exnase II to obtain a ligation product; the ligation product was transformed into competent cells of *Escherichia coli* DH5a; the transformed competent cells of *Escherichia coli* DH5a were spread on an LB solid culture medium (containing 100 μg/mL ampicillin) and subjected to inverted culture at 37° C. for 24 hours; positive transformants were picked, plasmids were extracted, and a recombinant plasmid PMA5-fae was obtained after correct sequencing verification; the obtained recombinant plasmid PMA5-fae was transformed into *Bacillus subtilis* WB800 to obtain a transformation product; the transformation product was spread on an LB solid culture medium (containing 100 μg/mL kanamycin) and subjected to inverted culture in a constant-temperature incubator at 37°

C. for 8-12 hours to obtain a transformant; the transformant was subjected to PCR verification, and recombinant *Bacillus subtilis* WB800/PMA5-fae was obtained after correct verification.

The primers are as follows:

```
fae-F:
                                   (SEQ ID NO: 4)
aaaaggagcgatttacatatgATGAAC TTACAAGAGCAAATCAAAATCGCTGC;
and fae-R:
                                   (SEQ ID NO: 5)
gagctcgactctagaggatccTTAATG

GTGATGGTGATGATGTTCAAATGCCTTT.
```

Example 7: Production of a Feruloyl Esterase

Specific steps are as follows:

A transformant of recombinant *Bacillus subtilis* WB800/PMA5-fae obtained in Example 1 was streaked on an LB solid culture medium (containing 100 μg/mL kanamycin) and subjected to inverted culture in a constant-temperature incubator at 30° C. for 12 hours to obtain a single colony; the single colony was picked, and an LB liquid culture medium (containing 100 μg/mL kanamycin) was inoculated with the single colony for culturing at 37° C. and 200 r/min for 12 hours to obtain a seed solution; a Super Rich culture medium was inoculated with the seed solution according to an inoculation amount of 3% (v/v) for culturing at 37° C. and 200 r/min for 60 hours to obtain a fermentation solution.

1 mL of the fermentation solution was sampled at regular intervals during fermentation; the fermentation solution was centrifuged at 4° C. and 10,000 rpm for 15 minutes to obtain a fermentation supernatant and a precipitate; 1 mL of a lysis solution was added into the precipitate for resuspending bacterial cells to obtain a resuspension solution (whole cells).

The enzyme activity of the feruloyl esterase in the fermentation supernatants and resuspension solutions obtained after different fermentation times is detected (detection results are shown in Table 2), and a detection method is as follows:

10 μL of the fermentation supernatant or resuspension solution was added into 990 μL of a methyl ferulate solution with a concentration of 0.003 mol/L to obtain an enzyme reaction system (the methyl ferulate solution was obtained by dissolving methyl ferulate in a Tris-HCl buffer solution with a pH of 8.0 and a concentration of 0.05 mol/L); the enzyme reaction system was subjected to a reaction in a water bath pot at 50° C. for 10 minutes and enzyme deactivation with boiling water for 10 minutes and then filtered with a 0.22 μm membrane to obtain a reaction solution; a crude enzyme solution obtained after enzyme inactivation was used as a blank control, and the concentration of ferulic acid in the reaction solution was detected by HPLC (high performance liquid chromatography); the concentration of ferulic acid was substituted into a calculation formula of the activity of the feruloyl esterase to obtain the enzyme activity of the feruloyl esterase in the crude enzyme solution.

It can be seen from Table 2 that when fermentation is performed for 14 hours, the enzyme activity of the feruloyl esterase in the resuspension solution obtained by fermentation of recombinant *Bacillus subtilis* WB800/PMA5-fae reaches 3.20 U/mL; when fermentation is performed for 60 hours, the enzyme activity of the feruloyl esterase in the fermentation supernatant obtained by fermentation of recombinant *Bacillus subtilis* WB800/PMA5-fae reaches 20.80 U/mL; when fermentation is performed for 14 hours or above, the enzyme activity of the feruloyl esterase in the resuspension solution obtained by fermentation of recombinant *Bacillus subtilis* WB800/PMA5-fae is first reduced and then improved; when fermentation is performed for 40 hours or above, the enzyme activity of the feruloyl esterase in the fermentation supernatant obtained by fermentation of recombinant *Bacillus subtilis* WB800/PMA5-fae is constantly improved.

TABLE 2

The enzyme activity of the feruloyl esterase in the fermentation supernatants and resuspension solutions obtained after different fermentation times

| Group | Fermentation supernatant (U/mL) | Resuspension solution (U/mL) |
|---|---|---|
| Fermentation for 6 hours | 0.20 | 0.17 |
| Fermentation for 14 hours | 2.13 | 3.20 |
| Fermentation for 20 hours | 1.24 | 1.01 |
| Fermentation for 25 hours | 10.01 | 1.51 |
| Fermentation for 37 hours | 17.92 | 1.94 |
| Fermentation for 42 hours | 15.10 | 2.27 |
| Fermentation for 48 hours | 16.15 | 1.86 |
| Fermentation for 54 hours | 18.81 | 1.45 |
| Fermentation for 60 hours | 20.80 | 1.60 |

Example 8: Production of a Feruloyl Esterase

Specific steps are as follows:

*Bacillus subtilis* WB800 was used as a contrast, and a transformant of recombinant *Bacillus subtilis* WB800/PMA5-fae obtained in Example 7 was streaked on an LB solid culture medium (containing 100 μg/mL kanamycin) and subjected to inverted culture in a constant-temperature incubator at 30° C. for 12 hours to obtain a single colony; the single colony was picked, and an LB liquid culture medium (containing 100 μg/mL kanamycin) was inoculated with the single colony for culturing at 37° C. and 200 r/min for 12 hours to obtain a seed solution; a Super Rich culture medium was inoculated with the seed solution according to an inoculation amount of 3% (v/v) and cultured at 37° C. and 200 r/min for 14 hours to obtain a fermentation solution.

After fermentation was completed, 5 mL of the fermentation solution was taken and centrifuged at 4° C. and 8,000 rpm for 15 minutes to obtain a fermentation supernatant and a precipitate; 5 mL of a lysis solution was added into the precipitate for resuspending bacterial cells to obtain a resuspension solution (whole cells); the resuspension solution was subjected to ultrasonication for 15 minutes to obtain a cell disruption solution; the cell disruption solution was centrifuged at 4° C. and 8,000 rpm for 15 minutes to obtain a cell disruption supernatant.

The enzyme activity of the feruloyl esterase in the fermentation supernatants and cell disruption supernatants obtained by fermentation of *Bacillus subtilis* WB800 and recombinant *Bacillus subtilis* WB800/PMA5-fae is detected (detection results are shown in Table 3).

It can be seen from Table 3 that when fermentation is performed for 14 hours, the enzyme activity of the intracellular feruloyl esterase obtained by fermentation of recombinant *Bacillus subtilis* WB800/PMA5-fae is 82.53 U/mL and is 4 times higher than 20.80 U/mL which is the enzyme activity of the extracellular feruloyl esterase when fermentation is performed for 60 hours; at the same time, the activity of the intracellular feruloyl esterase of recombinant *Bacillus subtilis* WB800/PMA5-fae is significantly higher than that of the intracellular feruloyl esterase of *Bacillus subtilis* WB800. Therefore, the intracellular feruloyl esterase after fermentation is performed for 14 hours is used as a basis for subsequent enzyme purification.

TABLE 3

The enzyme activity of the feruloyl esterase in the fermentation supernatants and cell disruption supernatants obtained by fermentation of different kinds of *Bacillus subtilis*

| *Bacillus subtilis* WB800 | | Recombinant *Bacillus subtilis* WB800/PMA5-fae | |
|---|---|---|---|
| Fermentation supernatant | Cell disruption supernatant | Fermentation supernatant | Cell disruption supernatant |
| 0.85 U/mL | 2.08 U/mL | 2.13 U/mL | 82.53 U/mL |

Example 9: Performance of a Feruloyl Esterase

Specific steps are as follows:

A cell disruption supernatant obtained by fermentation of recombinant *Bacillus subtilis* WB800/PMA5-fae obtained in Example 3 was purified with a nickel column, dialyzed three times with a dialysis solution containing 0.01 mol/L EDTA and then dialyzed three times with a dialysis solution without EDTA to obtain a pure enzyme; the pure enzyme was placed in a refrigerator at 4° C. for later use.

After the pure enzyme is diluted 0-50 times, the enzyme activity of the feruloyl esterase in the pure enzyme is detected according to the method in Example 5, and detection results are shown in Table 4.

It can be seen from Table 4 that a dilution multiple of 20 times is the best choice; the enzyme activity of the feruloyl esterase in the pure enzyme diluted 20 times is detected, and a detection method is as follows:

100 mg of coomassie brilliant blue G-250 was weighed and dissolved in 50 mL of 90% (v/v) ethanol, 100 mL of 85% (v/v) phosphoric acid was added, and the mixture was diluted with distilled water to 1 L to obtain a coomassie brilliant blue G-250 dyeing solution; 100 mg of bovine albumin was weighed, dissolved and diluted with distilled water to 100 mL to obtain a standard protein solution; 0, 0.02, 0.04, 0.06, 0.08 and 0.10 mL of the standard protein solution were sucked and added into 1.0, 0.98, 0.96, 0.94, 0.92 and 0.90 mL of distilled water respectively, and 5 mL of the coomassie brilliant blue G-250 dyeing solution was separately added into the solutions and mixed uniformly to obtain mixed solutions; the mixed solutions were subjected to a reaction at room temperature (25° C.) for 5 minutes to obtain reaction solutions; the absorbance of the reaction solutions was detected at a wavelength of 595 nm, and a protein concentration standard curve was drawn (the standard curve is shown in FIG. 7).

500 µL of distilled water and 5 mL of the coomassie brilliant blue G-250 dyeing solution were sequentially added into 500 µL of the pure enzyme and then uniformly mixed to obtain a mixed solution; the mixed solution was subjected to a reaction at room temperature (25° C.) for 5 minutes to obtain a reaction solution; the absorbance of the reaction solution was detected at a wavelength of 595 nm; the concentration of protein in the pure enzyme was calculated based on the detected absorbance and the protein concentration standard curve, and the specific enzyme activity of the feruloyl esterase was calculated based on the activity of the feruloyl esterase in the pure enzyme diluted 20 times.

A calculation formula of the specific enzyme activity of the feruloyl esterase is as follows:

specific enzyme activity=enzyme activity of crude enzyme solution/concentration of protein.

According to detection results, the concentration of protein in the pure enzyme diluted 20 times is 0.15 mg/mL, and the specific enzyme activity of the feruloyl esterase in the pure enzyme diluted 20 times is 2230 U/mg.

TABLE 4

The enzyme activity of the feruloyl esterase in the pure enzymes diluted different times

| Dilution multiple of pure enzyme | Volume of added enzyme (after dilution)/µL | Enzyme activity (U/mL) | Note |
|---|---|---|---|
| 0 | 10 | 47.85 | A reaction of a substrate is complete |
| 2 | 10 | 60.53 | A reaction of a substrate is almost complete |
| 5 | 10 | 142.25 | A reaction of a substrate is almost complete |
| 20 | 10 | 334.50 | A peak height ratio is 4:3 |
| 50 | 10 | 210.89 | A peak height ratio is 1:4 |

Although the disclosure has been disclosed above in preferred examples, the examples are not intended to limit the disclosure. Various changes and modifications can be made by those skilled in the art without departing from the spirit and scope of the disclosure. Therefore, the protection scope of the disclosure should be defined by the claims.

What is claimed is:

1. A microbial cell, wherein the cell comprises:
   a gene encoding a feruloyl esterase having the amino acid sequence set forth in SEQ ID NO:2,
   a recombinant plasmid comprising the gene,
   wherein the recombinant plasmid is a pMA5 plasmid or a pTSC plasmid.

2. The microbial cell according to claim 1, wherein the nucleotide sequence of the gene is SEQ ID NO:3.

3. The microbial cell according to claim 1, wherein the microbial cell is *Bacillus pumilus* or *Bacillus subtilis*.

4. The microbial cell according to claim 3, wherein the *Bacillus subtilis* is *Bacillus subtilis* 168, *Bacillus subtilis* WB800, *Bacillus subtilis* WB600 or *Bacillus subtilis* 1A751.

* * * * *